US008148325B2

(12) United States Patent
Yamka et al.

(10) Patent No.: US 8,148,325 B2
(45) Date of Patent: Apr. 3, 2012

(54) METHODS FOR ENHANCING THE QUALITY OF LIFE OF A SENIOR ANIMAL

(75) Inventors: Ryan Yamka, Topeka, KS (US); Kim Gene Friesen, Topeka, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 770 days.

(21) Appl. No.: 11/813,276

(22) PCT Filed: Dec. 30, 2005

(86) PCT No.: PCT/US2005/047461
§ 371 (c)(1),
(2), (4) Date: Mar. 28, 2008

(87) PCT Pub. No.: WO2006/074089
PCT Pub. Date: Jul. 13, 2006

(65) Prior Publication Data
US 2008/0206398 A1    Aug. 28, 2008

Related U.S. Application Data

(60) Provisional application No. 60/640,890, filed on Dec. 30, 2004.

(51) Int. Cl.
| A61K 38/00 | (2006.01) |
| A61K 31/34 | (2006.01) |
| A61K 31/22 | (2006.01) |
| A61K 31/20 | (2006.01) |
| A23K 1/00  | (2006.01) |

(52) U.S. Cl. ......... 514/2.1; 514/474; 514/549; 514/560; 426/635

(58) Field of Classification Search .................. 426/635; 514/2, 474, 549, 560
See application file for complete search history.

(56) References Cited

U.S. PATENT DOCUMENTS

| 2,980,716 A | 4/1961 | Reed |
| 3,202,514 A | 8/1965 | Burgess et al. |
| 3,946,123 A | 3/1976 | Hanna |
| 4,053,647 A | 10/1977 | Prussin |
| 4,247,562 A | 1/1981 | Bernotavicz |
| 4,898,890 A | 2/1990 | Sato et al. |
| 4,997,671 A | 3/1991 | Spanier |
| 4,997,672 A | 3/1991 | DeSimone et al. |
| 5,004,624 A | 4/1991 | Koschak et al. |
| 5,030,458 A | 7/1991 | Shug et al. |
| 5,114,704 A | 5/1992 | Spanier et al. |
| 5,118,505 A | 6/1992 | Koltringer |
| 5,292,538 A | 3/1994 | Paul et al. |
| 5,339,771 A | 8/1994 | Axelrod |
| 5,419,283 A | 5/1995 | Leo |
| 5,455,264 A | 10/1995 | Beisswenger et al. |
| 5,532,010 A | 7/1996 | Spanier et al. |
| 5,569,670 A | 10/1996 | Weischer et al. |
| 5,599,835 A | 2/1997 | Fischer |
| 5,621,117 A | 4/1997 | Bethge et al. |
| 5,624,896 A | 4/1997 | Axworthy |
| 5,723,441 A | 3/1998 | Higley et al. |
| 5,728,735 A | 3/1998 | Ulrich et al. |
| 5,730,988 A | 3/1998 | Womack |
| 5,756,088 A | 5/1998 | Matsuura et al. |
| 5,851,573 A | 12/1998 | Lepine et al. |
| 5,858,024 A | 1/1999 | De Lacharriere et al. |
| 5,883,083 A | 3/1999 | Harless |
| 5,916,912 A | 6/1999 | Ames et al. |
| 5,932,257 A | 8/1999 | Wright et al. |
| 5,976,548 A | 11/1999 | Hsia et al. |
| 5,976,568 A | 11/1999 | Riley |
| 5,977,162 A | 11/1999 | Seidman |
| 5,981,767 A | 11/1999 | Tanner et al. |
| 5,994,393 A | 11/1999 | Beisswenger et al. |
| 6,039,952 A | 3/2000 | Sunvold et al. |
| 6,080,788 A | 6/2000 | Sole et al. |
| 6,090,414 A | 7/2000 | Passwater |
| 6,117,477 A | 9/2000 | Paluch |
| 6,133,323 A | 10/2000 | Hayek |
| 6,136,339 A | 10/2000 | Gardiner |
| 6,136,859 A | 10/2000 | Hienriksen |
| 6,184,227 B1 | 2/2001 | Karmali |
| 6,190,591 B1 | 2/2001 | Van Lengerich |
| 6,194,454 B1 | 2/2001 | Dow |
| 6,197,340 B1 | 3/2001 | Byrd et al. |
| 6,232,346 B1 | 5/2001 | Sole et al. |
| 6,264,994 B1 | 7/2001 | Castillo et al. |
| 6,277,842 B1 | 8/2001 | Carthron |
| 6,306,392 B1 | 10/2001 | Cavazza |
| 6,306,442 B1 | 10/2001 | Sunvold et al. |

(Continued)

FOREIGN PATENT DOCUMENTS

CN    1469712    1/2004

(Continued)

OTHER PUBLICATIONS

Hornstra, Gerard et al., "Essential fatty acids in pregnancy and early human development," European Journal of Obstetrics & Gynecology and Reproductive Biology (1995) 61:57-62.

Lim, Sun-Young et al., "Intakes of Dietary Docosahexaenoic Acid Ethyl Ester and Egg Phosphatidylcholine Improve Maze-Learning Ability in Young and Old Mice," American Society For Nutritional Sciences (2000) 130 pps. 1629-1632.

International Search Report dated May 10, 2007.

Araujo et al; "Assessment of Nutritional Interventions for Modification of Age-Associated Cognitive Decline Using a Canine Model of Human Aging"; Age: Journal of the American Aging Association; 2005; pp. 27-37; 27:1.

(Continued)

*Primary Examiner* — Raymond Henley, III
(74) *Attorney, Agent, or Firm* — Shannon E. McGarrah

(57) ABSTRACT

Methods for enhancing the quality of life of a senior or super senior animals by feeding the animal a composition comprising at least one omega-3 polyunsaturated fatty acid and various combinations of amino acids, minerals, and antioxidants in amounts effective to enhance alertness, improve vitality, protect cartilage, maintain muscle mass, enhance digestibility, and improve skin and pelage quality.

18 Claims, No Drawings

U.S. PATENT DOCUMENTS

| | | |
|---|---|---|
| 6,310,090 B1 | 10/2001 | Hayek |
| 6,335,361 B1 | 1/2002 | Hamilton |
| 6,365,211 B1 | 4/2002 | Corrigan |
| 6,365,622 B1 | 4/2002 | Cavazza |
| 6,365,623 B1 | 4/2002 | Perricone |
| 6,379,727 B1 | 4/2002 | Addy |
| 6,426,362 B1 | 7/2002 | Miller et al. |
| 6,441,024 B1 | 8/2002 | Klatt et al. |
| 6,447,989 B1 | 9/2002 | Comper |
| 6,448,287 B1 | 9/2002 | Casciari |
| 6,458,767 B1 | 10/2002 | Murphy-Ullrich et al. |
| 6,479,069 B1 | 11/2002 | Hamilton |
| 6,492,325 B1 | 12/2002 | Cosgrove |
| 6,517,877 B2 | 2/2003 | Gannon |
| 6,572,888 B2 | 6/2003 | Byrd |
| 6,572,899 B1 | 6/2003 | Gorsek |
| 6,589,748 B2 | 7/2003 | Comper |
| 6,596,762 B2 | 7/2003 | Sokol |
| 6,599,876 B2 | 7/2003 | Kojima |
| 6,746,678 B1 | 6/2004 | Shapiro |
| 6,784,159 B2 | 8/2004 | Holub et al. |
| 6,902,739 B2 | 6/2005 | McPeak et al. |
| 6,914,071 B2 | 7/2005 | Zicker et al. |
| 6,974,841 B1 | 12/2005 | Rapisarda |
| 7,202,270 B2 | 4/2007 | Majeed et al. |
| 7,282,225 B1 | 10/2007 | Davis et al. |
| 2001/0043983 A1 | 11/2001 | Hamilton |
| 2001/0044448 A1 | 11/2001 | Dib |
| 2002/0006907 A1 | 1/2002 | Gardiner et al. |
| 2002/0028762 A1 | 3/2002 | Kojima |
| 2002/0052402 A1 | 5/2002 | Zicker et al. |
| 2002/0076469 A1 | 6/2002 | Zicker et al. |
| 2002/0076470 A1 | 6/2002 | Zicker et al. |
| 2002/0110582 A1 | 8/2002 | Place et al. |
| 2002/0115710 A1 | 8/2002 | Zicker et al. |
| 2002/0119182 A1 | 8/2002 | Zicker et al. |
| 2002/0183382 A1 | 12/2002 | Sokol |
| 2003/0000477 A1 | 1/2003 | Abril |
| 2003/0007998 A1 | 1/2003 | Block et al. |
| 2003/0035821 A1 | 2/2003 | Heaton |
| 2003/0044466 A1 | 3/2003 | Markey |
| 2003/0060503 A1 | 3/2003 | Hamilton |
| 2003/0068309 A1 | 4/2003 | De Simone |
| 2003/0138477 A1 | 7/2003 | Barclay |
| 2003/0194478 A1 | 10/2003 | Davenport et al. |
| 2003/0198730 A1 | 10/2003 | Stewart |
| 2003/0224061 A1 | 12/2003 | Pacioretty |
| 2004/0037944 A1 | 2/2004 | Cupp et al. |
| 2004/0047896 A1 | 3/2004 | Malnoe et al. |
| 2004/0068040 A1 | 4/2004 | Zicker et al. |
| 2004/0105879 A1 | 6/2004 | Heaton et al. |
| 2004/0166157 A1 | 8/2004 | Thombre |
| 2005/0026225 A1 | 2/2005 | Comper |
| 2005/0100617 A1 | 5/2005 | Malnoe et al. |
| 2005/0123628 A1 | 6/2005 | Zabrecky |
| 2005/0232976 A1 | 10/2005 | Zicker et al. |
| 2005/0249787 A1 | 11/2005 | Reynolds et al. |
| 2005/0266051 A1 | 12/2005 | Kelley |
| 2005/0266052 A1 | 12/2005 | Bartlett et al. |
| 2006/0002985 A1 | 1/2006 | Zicker et al. |
| 2006/0134014 A1 | 6/2006 | Scherl et al. |
| 2006/0141011 A1 | 6/2006 | Jewell |
| 2007/0264287 A1 | 11/2007 | Zicker et al. |
| 2008/0038323 A1 | 2/2008 | Zicker et al. |
| 2008/0057039 A1 | 3/2008 | Rogers et al. |
| 2008/0069834 A1 | 3/2008 | Zicker et al. |
| 2008/0206398 A1 | 8/2008 | Yamka |
| 2008/0214653 A1 | 9/2008 | Zicker et al. |
| 2008/0299286 A1 | 12/2008 | Josephson et al. |
| 2008/0317725 A1 | 12/2008 | Baum |
| 2008/0317884 A1 | 12/2008 | Jewell |
| 2009/0004299 A1 | 1/2009 | Wedekind et al. |
| 2009/0047361 A1 | 2/2009 | Jewell |
| 2009/0111877 A1 | 4/2009 | Yamka |
| 2009/0149529 A1 | 6/2009 | Zicker et al. |
| 2009/0155393 A1 | 6/2009 | Zicker et al. |
| 2009/0156658 A1 | 6/2009 | Zicker et al. |
| 2009/0176864 A1 | 7/2009 | Zicker et al. |
| 2009/0182032 A1 | 7/2009 | Zicker et al. |
| 2009/0227665 A1 | 9/2009 | Zicker et al. |
| 2009/0227666 A1 | 9/2009 | Jewell |
| 2010/0076064 A1 | 3/2010 | Zicker et al. |

FOREIGN PATENT DOCUMENTS

| | | |
|---|---|---|
| EP | 0678247 | 10/1995 |
| EP | 1155627 | 11/2001 |
| EP | 1350435 | 10/2003 |
| GB | 2027577 | 2/1980 |
| JP | S55-19090 | 2/1980 |
| JP | S57-132849 | 8/1982 |
| JP | H08-38063 | 2/1996 |
| JP | 2003-527124 | 9/2003 |
| JP | 2004-141130 | 5/2004 |
| RU | 2131677 | 6/1999 |
| RU | 2221456 | 1/2004 |
| WO | WO 97/13415 | 4/1997 |
| WO | WO 00/18247 | 4/2000 |
| WO | WO 2004/024930 | 3/2004 |
| WO | WO 2005/051093 | 6/2005 |
| WO | WO 2006/074089 | 7/2006 |
| WO | WO 2007/002837 | 1/2007 |
| WO | WO 2007/059439 | 5/2007 |
| WO | WO 2009/088433 | 7/2009 |

OTHER PUBLICATIONS

Hall et al; "Dietary (n-3) Fatty Acids Alter Plasma Fatty Acids and Leukotriene B Synthesis by Stimulated Neutrophils from Healthy Geriatric Beagles"; Prostaglandins Leukotrienes and Essential Fatty Acids; 2005; pp. 335-341; 73:5.

Hornstra et al; "Essential Fatty Acids in Pregnancy and Early Human Development"; European Journal of Obstetrics & Gynecology and Reproductive Biology; 1995; pp. 57-62.

Hossain, et al; "Antioxidative Effects of Docosahexaenoic Acid in the Cerebrum Versus the Cerebellum and Brainstem of Aged Hyperchlesterolemic Rats", Journal of Neurochemistry (1-99), pp. 1133-1138, vol. 72 (1999).

International Search Report of the International Searching Authority dated May 10, 2007 for International Application No. PCT/US2005/047461.

Kearns et al; "Effect of Age, Breed and Dietary Omega-6 (n-6): Omega-3 (n-3) Fatty Acid Ratio on Immune Function, Eicosadoid Production and Lipid Peroxidation in Young and Aged Dogs"; Veterinary Immunology and Immunopathology; 1999; pp. 165-183; vol. 69.

Rogers; "A Healthy Body, a Healthy Mind: Long-term Impact of Diet on Mood and Cognitive Function"; Proceedings of the Nutrition Society; vol. 60, 2001; pp. 135-143.

Michel; "Interventional Nutrition for the Critical Care Patient: Optimal Diets"; Clinical Techniques in Small Animal Practice; 1998; vol. 13, No. 4; pp. 204-210.

METHODS FOR ENHANCING THE QUALITY OF LIFE OF A SENIOR ANIMAL

CROSS-REFERENCE TO RELATED APPLICATIONS

This application is a national stage application of Patent Cooperation Treaty Patent Application No. PCT/US05/47461, filed Dec. 30, 2005, which claims priority to U.S. Provisional Application Ser. No. 60/640,890, filed Dec. 30, 2004, the contents of each is incorporated herein by reference.

BACKGROUND OF THE INVENTION

1. Field of the Invention

The present invention relates generally to methods for enhancing the quality of life of an animal and particularly to using food compositions containing omega-3 polyunsaturated fatty acids for enhancing the quality of life of a senior or super senior animal.

2. Description of the Related Art

Companion animals such as dogs and cats frequently require differing diets depending on their life stage (age), size, body composition, and breed. Both dog and cat nutrient requirements can be separated into three different categories, based on age: growing dogs (or cats), adult dogs (or cats), and senior dogs (or cats). The latter category, senior dogs (or cats), can be further separated into two stages, which include senior (or mature adult) and super senior (or geriatric). Dogs are further separated into different categories for regular breed dogs versus large-breed dogs.

Essential fatty acids, consisting of omega-3 and omega-6 polyunsaturated fatty acids, are critical nutrients for the health of an animal. These nutrients, however, either cannot be made by animals or cannot be made in sufficient amounts to elicit benefits and therefore must be consumed in an animal's diet. See, e.g., Hornstra, G., et al., "Essential fatty acids in pregnancy and early human development", Eur. J. Obs. & Gyn. and Reprod. Biology, 61:57-62 (1995). It has previously been postulated that Docosahexaenoic Acid ("DHA"), an omega-3 polyunsaturated fatty acid, is effective in increasing the maze-learning ability and brain functions in aged mice. See, Lim, S.-Y., "Intakes of dietary docosahexaenoic acid ethyl ester and egg phosphatidylcholine improve maze-learning ability in young and old mice", J. Nutr., 130:1629-1632 (2000).

Rogers discusses the theory of the potential use of antioxidants to slow the deterioration of cognitive function, particularly in the elderly. See Rogers, P., "A healthy body, a healthy mind: long-term impact of diet on mood and cognitive function", Proceedings of the Nutrition Society, 60:135-143 (2001).

Despite the studies and developments relating to improving cognitive abilities, there continues to be a need for methods for enhancing the quality of life of senior animals, as measured by enhanced alertness, improved vitality, protected cartilage, maintenance of muscle mass, enhanced digestibility, and improved skin and pelage quality in senior and super senior animals.

SUMMARY OF THE INVENTION

The invention provides methods for improving the quality of life of senior and super senior animals by feeding the animal a composition comprising at least about 9% by weight protein, at least about 5% by weight fat, and at least about 0.05% by weight of at least one omega-3 polyunsaturated fatty acid.

In one embodiment, the method comprises feeding the animal an amount of a composition effective to enhance the animal's quality of life, wherein enhanced quality of life is evidenced by improvement in one or more characteristics selected from the group consisting of alertness, vitality, cartilage protection, muscle mass maintenance, digestibility, and skin and pelage quality.

In another embodiment, the method comprises feeding the animal a composition comprising at least one omega-3 polyunsaturated fatty acid selected from the group consisting of docosahexaenoic acid ("DHA") and eicosapentaenoic acid ("EPA"). In an additional embodiment, the method comprises feeding the animal a composition further comprising at least one antioxidant and at least one nutrient selected from the group consisting of choline, manganese, methionine, cysteine, L-carnitine, lysine, and mixtures thereof.

Other and further objects, features, and advantages of the present invention will be readily apparent to those skilled in the art.

DETAILED DESCRIPTION OF THE INVENTION

Definitions

The terms "senior" or "mature adult" refers to the life-stage of an animal. For small or regular breed canines, the "senior" life stage is from about 7 to about 10 years of age. For felines, the "senior" life stage is from about 7 to about 12 years of age. For large breed canines, over 5 years of age represents "super senior" as described below.

The terms "super senior" or "geriatric" refers to a specific life-stage of an animal. For small or regular breed canines, the super senior stage is any age greater than 10 years of age. For large breed canines, the super senior stage is any age greater than 5 years of age. For felines, the super senior stage is any age greater than 12 years of age.

The term "large breed" canine means a canine that weighs more than 55 pounds when an adult.

The term "antioxidant" means a substance that is capable of reacting with free radicals and neutralizing them. Illustrative examples of such substances include beta-carotene, selenium, coenzyme Q10 (ubiquinone), luetin, tocotrienols, soy isoflavones, S-adenosylmethionine, glutathione, taurine, N-acetylcysteine, vitamin E, vitamin C, lipoic acid and L-carnitine. Examples of foods containing useful levels of one or more antioxidants include but are not limited to ginkgo biloba, green tea, broccoli, citrus pulp, grape pomace, tomato pomace, carrot spinach, and a wide variety of fruit meals and vegetable meals.

The Invention

The present invention provides methods for improving the quality of life of a senior or super senior animal. The methods comprise feeding the animal a composition comprising at least about 9% by weight protein, at least about 5% by weight fat, and at least about 0.05% by weight omega-3 polyunsaturated fatty acid. The methods are useful for enhancing alertness, improving vitality, protecting cartilage, maintaining muscle mass, enhancing digestibility, and improving skin and pelage quality in a senior or super senior animal. Without being bound by theory, the benefits of the invention may be the result of physiological effects from the addition of omega-3 polyunsaturated fatty acids to a senior or super senior animal's diet. Similarly, the antioxidants, choline, and other nutrients may play a role in enhancing a senior or super senior animal's quality of life.

As used herein, "enhanced quality of life" is defined as an improvement in one or more characteristics selected from the group consisting of alertness, vitality, protection of cartilage, maintenance of muscle mass, digestibility, and skin and pelage quality. Although the methods of the present invention may improve an animal's quality of life by enhancing all of the above characteristics including alertness, vitality, protection of cartilage, maintenance of muscle mass, digestibility, and skin and pelage quality, it is not necessary to demonstrate substantial improvements in each of the characteristics to achieve the "enhanced quality of life" as defined herein.

When the compositions are administered to a senior or super senior animal, the animal experiences an enhanced quality of life, e.g., exhibits or experiences one or more of enhanced alertness, improved vitality, protected cartilage, maintained muscle mass, enhanced digestibility, and improved skin and pelage quality. Methods for determining these measurements of quality of life are known to skilled artisans. For example, alertness can be measured by various means, including an analysis of metabolism and antioxidant markers, as well as through clinical studies with follow-up questions to participating pet owners. Potential metabolism markers may include ghrelin, GLP-1, thyroid hormone, and/or growth hormone. Potential markers of antioxidant status may include serum vitamin E, ORAC, glutathione peroxidase, alkanels, and/or cell damage indicators. Further, vitality can be measured by various means, including an analysis of metabolism and antioxidant markers, as well as through clinical studies with follow-up questions to participating pet owners. Similarly, cartilage protection can be measured by various means, including an analysis of arthritis biomarkers. Potential arthritis biomarkers may include type II collagen synthesis, matric metaloproteinase, osteocalcin, alkaline phosphatase activity, COMP, and fragments of cartilage damage. Muscle mass maintenance can be measured by various means, including an analysis of body composition and digestibility can be measured by various means, including clinical studies with follow-up questions to participating pet owners and animal feeding to determine the percentage of nutrients digested. Skin and pelage quality can be measured by various means, including clinical studies with follow-up questions to participating pet owners.

The methods of the invention are useful for enhancing the quality of life for a variety of animals, including non-human animals such as non-human primates (e.g., monkeys, chimpanzees, etc.), companion animals (e.g., dogs, cats, horses, etc.), farm animals (e.g., goats, sheep, swine, cattle, etc.), laboratory animals (e.g., mice, rats, etc.), birds (e.g., domestic birds such as canaries, parrots, etc. and commercial birds such as chickens, ducks, turkeys, etc.), rodents (e.g., hamsters, guinea pigs, gerbils, rabbits, hedgehogs, ferrets, chinchillas, etc.), and wild, exotic, and zoo animals (e.g., wolves, bears, deer, etc.). In various embodiments, the animal is a cat, a dog, or a horse.

The compositions of the present invention are designed to enhance digestibility improve chewability. Canine and feline foods are typically formulated based on life stage (age), size, body composition, and breed. Thus, some embodiments of the present invention include compositions that are formulated to address specific nutritional differences between regular or small breed dogs, large breed dogs, and cats.

The invention provides methods utilizing a variety of compositions containing at least one omega-3 polyunsaturated fatty acid. The compositions include foods, supplements, treats, and toys (typically chewable and consumable toys). The methods also provide the compositions to the designated animals over a period of time that is long enough to effectuate the improved quality of life. In one embodiment, the method provides the animal with a composition for at least thirty days.

The compositions for use in the methods of the present invention generally have an omega-3 polyunsaturated fatty acid content of at least about 0.02% (or from about 0.05% to about 10%, or from about 0.1% to about 6%) by weight on a dry matter basis. In some embodiments, the omega-3 polyunsaturated fatty acid is DHA. In other embodiments, the omega-3 polyunsaturated fatty acid is EPA. In still other embodiments, the omega-3 polyunsaturated fatty acid comprises a mixture of DHA and EPA.

In some embodiments, the composition containing omega-3 polyunsaturated fatty acid is a food. Although both liquid and solid foods are provided, solid foods are typically preferred. Foods include both dry foods and wet foods. Some of the non-polyunsaturated fatty acid components of the food, and their preferred proportions, include those listed in Table 1.

TABLE 1

| Component | Proportion of the composition (% of dry weight of composition or parts per million) |
|---|---|
| Protein | from about 9% to about 55%, or from about 18% to about 30%, or from about 33% to about 55% or from about 18% to about 20% or from about 33% to about 36% |
| Fat | from about 7% to about 35%, or from about 18% to about 35%, or from about 7% to about 24%, or from about 14% to about 24%, or from about 14% to about 16% or from about 18% to about 24% |
| Antioxidant | from about 0 ppm to about 7500 ppm, or from about 0.05 ppm to about 3600 ppm, or from about 250 to about 3600, or from about 250 ppm to about 1650 ppm, or from about 5 ppm to about 225 ppm, or from about 0.05 ppm to about 2.4 ppm |

In one embodiment, the methods of this invention comprise feeding a super senior animal a composition in an amount effective to enhance the animal's quality of life. Such compositions generally comprise:
(a) 0.02% (or from about 0.05% to about 10%, or from about 0.1% to about 6%) at least one omega-3 polyunsaturated fatty acid, and
(b) at least one of the following:
  (i) from about 10% to about 55% (or from about 18% to about 30%, or from about 33% to about 55% or from about 18% to about 20% or from about 33% to about 36%) protein,
  (ii) from about 7% to about 35% (or from about 18% to about 35%, or from about 7% to about 24%, or from about 14% to about 24%, or from about 14% to about 16% or from about 18% to about 24%) fat, and
  (iii) at least about 0.05 (or from about 0.05 ppm to about 7500 ppm, or from about 250 to about 3600, or from about 250 ppm to about 1650 ppm, or from about 5 ppm to about 225 ppm, or from about 0.05 ppm to about 2.4 ppm) antioxidant.

In another embodiment, the methods of this invention comprise feeding a super senior regular breed canine a composition in an amount effective to enhance the canine's quality of life. The composition generally comprises:
(a) at least one of the following:
  (i) at least about 0.02% (or from about 0.02% to about 0.3%, or from about 0.05% to about 0.3%, or from about 0.05% to about 0.2%) DHA, and (ii) at least about 0.1% (or from about 0.1% to about 0.5%, or from about 0.2% to about 0.5%, or from about 0.2% to about 0.3%) EPA,
(b) at least about 9% (or from about 9% to about 30%, or from about 18% to about 30%, or from about 18% to about 20%) protein,
(c) at least about 7% (or from about 7% to about 24%, or from about 14% to about 24%, or from about 14% to about 16%) fat, and
(d) at least one of the following:
  (i) at least about 250 ppm (or from about 250 ppm to about 1500 ppm, or from about 500 ppm to about 1500 ppm, or from about 500 ppm to about 1000 ppm) vitamin E,
  (iv) at least about 50 ppm (or from about 50 ppm to about 500 ppm, or from about 100 ppm to about 500 ppm, or from about 100 ppm to about 301 ppm) vitamin C,
  (v) at least about 600 ppm (or from about 600 ppm to about 2400 ppm, or from about 1260 ppm to about 2400 ppm, or from about 1260 ppm to about 1545 ppm) taurine,
  (vi) at least about 50 ppm (or from about 50 ppm to about 200 ppm, or from about 100 to about 160, or from about 100 to about 155) lipoic acid, and
  (vii) at least about 150 ppm (or from about 150 ppm to about 500 ppm, or from about 200 ppm to about 500 ppm, or from about 200 ppm to about 350 ppm) carnitine.

In another embodiment, the methods of this invention comprise feeding a super senior large breed canine a composition in an amount effective to enhance the canine's quality of life. The compositions generally comprise:
(a) at least one of the following:
  (i) at least about 0.02% (or from about 0.02% to about 0.3%, or from about 0.05% to about 0.3%, or from about 0.05% to about 0.2%) DHA, and
  (ii) at least about 0.1% (or from about 0.1% to about 0.5%, or from about 0.2% to about 0.5%, or from about 0.2% to about 0.3%) EPA,
(b) at least about 9% (or from about 9% to about 30%, or from about 18% to about 30%, or from about 18% to about 20%) protein,
(c) at least about 7% (or from about 7% to about 24%, or from about 14% to about 24%, or from about 14% to about 16%) fat, and
(d) at least one of the following:
  (i) at least about 250 ppm (or from about 250 ppm to about 1500 ppm, or from about 500 ppm to about 1500 ppm, or from about 500 ppm to about 1000 ppm) vitamin E,
  (viii) at least about 50 ppm (or from about 50 ppm to about 500 ppm, or from about 100 ppm to about 500 ppm, or from about 100 ppm to about 301 ppm) vitamin C,
  (ix) at least about 600 ppm (or from about 600 ppm to about 2400 ppm, or from about 1260 ppm to about 2400 ppm, or from about 1260 ppm to about 1575 ppm) Taurine, and
  (x) at least about 50 ppm (or from about 50 ppm to about 200 ppm, or from about 100 to about 160, or from about 100 to about 155) lipoic acid, and
  (xi) at least about 150 ppm (or from about 150 ppm to about 500 ppm, or from about 200 ppm to about 500 ppm, or from about 200 ppm to about 350 ppm) carnitine.

In another embodiment, the methods of this invention comprise feeding a super senior feline a composition in an amount effective to enhance the feline's quality of life. The compositions generally comprise:
(a) at least one of the following:
  (i) at least about 0.05% (or from about 0.05% to about 0.30%, or from about 0.1% to about 0.30%, or from about 0.1% to about 0.2%) DHA, and
  (ii) at least about 0.1% (or from about 0.1% to about 0.5%, or from about 0.2% to about 0.5%, or from about 0.2% to about 0.3%) EPA,
(b) at least about 15% (or from about 15% to about 55%, or from about 30% to about 55%, or from about 33% to about 36%) protein,
(c) at least about 9% (or from about 9% to about 35%, or from about 18% to about 35%, or from about 18% to about 24%) fat, and
(d) at least one of the following:
  (i) at least about 250 ppm (or from about 250 ppm to about 1500 ppm, or from about 500 ppm to about 1500 ppm, or from about 500 ppm to about 1100 ppm) vitamin E,
  (xii) at least about 50 ppm (or from about 50 ppm to about 300 ppm, or from about 100 ppm to about 300 ppm, or from about 100 ppm to about 200 ppm) vitamin C,
  (xiii) at least about 1100 ppm (or from about 1100 ppm to about 3500 ppm, or from about 2300 ppm to about 3500 ppm, or from about 2300 ppm to about 2350 ppm) taurine, and
  (xiv) at least about 200 ppm (or from about 200 to about 750 ppm, or from about 400 ppm to about 750 ppm, or from about 400 to about 525 ppm) carnitine, and
  (xv) at least about 0.05% (or from about 0.05% to about 0.6%, or from about 0.1% to about 0.6%, or from about 0.1% to about 0.4%) cystine.

In another embodiment, the methods of this invention comprise feeding a super senior animal a composition in an amount effective to enhance the animal's alertness and vitality. The composition generally comprises:
(a) 0.02% (or from about 0.05% to about 10%, or from about 0.1% to about 6%) at least one omega-3 polyunsaturated fatty acid, and
(b) at least one of the following:
  (xvi) from about 10% to about 55% (or from about 18% to about 30%, or from about 33% to about 55% or from about 18% to about 20% or from about 33% to about 36%) protein,
  (xvii) from about 7% to about 35% (or from about 18% to about 35%, or from about 7% to about 24%, or from about 14% to about 24%, or from about 14% to about 16% or from about 18% to about 24%) fat,
  (xviii) at least about 0.05 (or from about 0.05 ppm to about 7500 ppm, or from about 250 to about 3600, or from about 250 ppm to about 1650 ppm, or from about 5 ppm to about 225 ppm, or from about 0.05 ppm to about 2.4 ppm) antioxidant, and
  (xix) at least about 1000 ppm (or from about 1000 ppm to about 5000 ppm, from about 3300 ppm to about 5000 ppm, or from about 2000 ppm to about 3000 ppm, or from about 3000 ppm to about 4000 ppm) choline.

In another embodiment, the methods of this invention comprise feeding a super senior regular breed canine a composition in an amount effective to enhance the canine's alertness and vitality. The composition generally comprises:
- (a) at least one of the following:
  - (i) at least about 0.02% (or from about 0.02% to about 0.3%, or from about 0.05% to about 0.3%, or from about 0.05% to about 0.2%) DHA, and
  - (ii) at least about 0.1% (or from about 0.1% to about 0.5%, or from about 0.2% to about 0.5%, or from about 0.2% to about 0.3%) EPA,
- (b) at least about 9% (or from about 9% to about 30%, or from about 18% to about 30%, or from about 18% to about 20%) protein,
- (c) at least about 7% (or from about 7% to about 24%, or from about 14% to about 24%, or from about 14% to about 16%) fat,
- (d) at least one of the following:
  - (i) at least about 250 ppm (or from about 250 ppm to about 1500 ppm, or from about 500 ppm to about 1500 ppm, or from about 500 ppm to about 1000 ppm) vitamin E,
  - (xx) at least about 50 ppm (or from about 50 ppm to about 500 ppm, or from about 100 ppm to about 500 ppm, or from about 100 ppm to about 301 ppm) vitamin C,
  - (xxi) at least about 600 ppm (or from about 600 ppm to about 2400 ppm, or from about 1260 ppm to about 2400 ppm, or from about 1260 ppm to about 1545 ppm) taurine, and
  - (xxii) at least about 50 ppm (or from about 50 ppm to about 200 ppm, or from about 100 to about 160, or from about 100 to about 155) lipoic acid, and
  - (xxiii) at least about 150 ppm (or from about 150 ppm to about 500 ppm, or from about 200 ppm to about 500 ppm, or from about 200 ppm to about 350 ppm) carnitine,
- (e) at least about 1000 ppm (or from about 1000 ppm to about 3200 ppm, or from about 2000 ppm to about 3200 ppm, or from about 2000 ppm to about 2500 ppm) choline,
- (f) at least about 50 ppm (or from about 50 ppm to about 150 ppm, or from about 100 ppm to about 150 ppm, or from about 100 ppm to about 110 ppm) manganese, and
- (g) at least about 0.4% (or from about 0.4% to about 2%, or from about 0.9% to about 2%, or from about 0.9% to about 1.2%) lysine, and
- (h) at least about 0.4% to about 1.5% methionine.

In another embodiment, the methods of this invention comprise feeding a super senior large breed canine a composition in an amount effective to enhance the canine's alertness and vitality. The composition generally comprises:
- (a) at least one of the following:
  - (i) at least about 0.02% (or from about 0.02% to about 0.3%, or from about 0.05% to about 0.3%, or from about 0.05% to about 0.2%) DHA, and
  - (ii) at least about 0.1% (or from about 0.1% to about 0.5%, or from about 0.2% to about 0.5%, or from about 0.2% to about 0.3%) EPA,
- (b) at least about 9% (or from about 9% to about 30%, or from about 18% to about 30%, or from about 18% to about 20%) protein,
- (c) at least about 7% (or from about 7% to about 24%, or from about 14% to about 24%, or from about 14% to about 16%) fat,
- (d) at least one of the following:
  - (i) at least about 250 ppm (or from about 250 ppm to about 1500 ppm, or from about 500 ppm to about 1500 ppm, or from about 500 ppm to about 1000 ppm) vitamin E,
  - (xxiv) at least about 50 ppm (or from about 50 ppm to about 500 ppm, or from about 100 ppm to about 500 ppm, or from about 100 ppm to about 301 ppm) vitamin C,
  - (xxv) at least about 600 ppm (or from about 600 ppm to about 2400 ppm, or from about 1260 ppm to about 2400 ppm, or from about 1260 ppm to about 1575 ppm) taurine, and
  - (xxvi) at least about 50 ppm (or from about 50 ppm to about 200 ppm, or from about 100 to about 160, or from about 100 to about 155) lipoic acid, and
  - (xxvii) at least about 150 ppm (or from about 150 ppm to about 500 ppm, or from about 200 ppm to about 500 ppm, or from about 200 ppm to about 350 ppm) carnitine.
- (e) at least about 1000 ppm (or from about 1000 ppm to about 3200 ppm, or from about 2000 ppm to about 3200 ppm, or from about 2000 ppm to about 2500 ppm) choline,
- (f) at least about 50 ppm (or from about 50 ppm to about 150 ppm, or from about 100 ppm to about 150 ppm, or from about 100 ppm to about 110 ppm) manganese, and
- (g) at least about 0.4% (or from about 0.4% to about 2%, or from about 0.9% to about 2%, or from about 0.9% to about 1.2%) lysine, and
- (h) at least about 0.4% to about 1.5% methionine.

In another embodiment, the methods of this invention comprise feeding a super senior feline a composition in an amount effective to enhance the feline's alertness and vitality. The composition generally comprises:
- (a) at least one of the following:
  - (i) at least about 0.05% (or from about 0.05% to about 0.30%, or from about 0.1% to about 0.30%, or from about 0.1% to about 0.2%) DHA, and
  - (ii) at least about 0.1% (or from about 0.1% to about 0.5%, or from about 0.2% to about 0.5%, or from about 0.2% to about 0.3%) EPA,
- (b) at least about 15% (or from about 15% to about 55%, or from about 30% to about 55%, or from about 33% to about 36%) protein,
- (c) at least about 9% (or from about 9% to about 35%, or from about 18% to about 35%, or from about 18% to about 24%) fat,
- (d) at least one of the following:
  - (i) at least about 250 ppm (or from about 250 ppm to about 1500 ppm, or from about 500 ppm to about 1500 ppm, or from about 500 ppm to about 1100 ppm) vitamin E,
  - (xxviii) at least about 50 ppm (or from about 50 ppm to about 300 ppm, or from about 100 ppm to about 300 ppm, or from about 100 ppm to about 200 ppm) vitamin C,
  - (xxix) at least about 1100 ppm (or from about 1100 ppm to about 3500 ppm, or from about 2300 ppm to about 3500 ppm, or from about 2300 ppm to about 2350 ppm) taurine, and
  - (xxx) at least about 200 ppm (or from about 200 to about 750 ppm, or from about 400 ppm to about 750 ppm, or from about 400 to about 525 ppm) carnitine, and
  - (xxxi) at least about 0.05% (or from about 0.05% to about 0.6%, or from about 0.1% to about 0.6%, or from about 0.1% to about 0.4%) cystine.

(e) at least about 1600 ppm (or from about 1600 ppm to about 5000 ppm, or from about 3300 ppm to about 5000 ppm, or from about 3300 ppm to about 3400 ppm) choline, (f) at least about 50 ppm (or from about 50 ppm to about 150 ppm, or from about 100 ppm to about 150 ppm, or from about 100 ppm to about 110 ppm) manganese, and (g) at least about 0.7% (or from about 0.7% to about 3%, or from about 1.4% to about 3%, or from about 1.4% to about 1.7%) lysine, and (h) at least about 0.4% to about 1.5% methionine.

In another embodiment, this invention provides a method for improving the quality of life of a senior or super senior small or regular breed canine. The method comprises feeding the canine a composition comprising:

from about 60% to about 70% by weight starch;
from about 15% to about 25% by weight protein selected from the group consisting of animal protein and vegetable protein;
from about 5% to about 7% by weight fat selected from the group consisting of animal fat and vegetable fat;
from about 2.5% to about 4% by weight of at least one omega-3 polyunsaturated fatty acids; from about 1% to about 2% by weight fiber;
from about 1% to about 2% by weight minerals; and
from about 0.5 to about 1.5% by weight vitamins.

In another embodiment, this invention provides a method for improving the quality of life of a senior or super senior large breed canine. The method comprises feeding the canine a composition comprising:

from about 60% to about 70% by weight starch;
from about 15% to about 25% by weight protein selected from the group consisting of animal protein and vegetable protein;
from about 5% to about 7% by weight fat selected from the group consisting of animal fat and vegetable fat;
from about 3% to about 5% by weight of at least one omega-3 polyunsaturated fatty acids;
from about 1% to about 1.5% by weight fiber;
from about 0.5% to about 1% by weight minerals; and
from about 0.75 to about 1.25% by weight vitamins.

In another embodiment, this invention provides a method for improving the quality of life of a senior or super senior feline. The method comprises feeding the feline a composition comprising:

from about 30% to about 35% by weight starch;
from about 40% to about 50% by weight protein selected from the group consisting of animal protein and vegetable protein;
from about 12% to about 15% by weight fat selected from the group consisting of animal fat and vegetable fat;
from about 1% to about 2% by weight of at least one omega-3 polyunsaturated fatty acids;
from about 3% to about 5% by weight fiber;
from about 1% to about 2% by weight minerals; and
from about 1% to about 2% by weight vitamins.

The compositions for use in the methods of this invention further comprise at least one nutrient selected from the group consisting of manganese, methionine, cysteine, mixtures of methionine and cysteine, L-carnitine, lysine, and arginine. Specific preferred amounts for each component in a composition will depend on a variety of factors including, for example, the species of animal consuming the composition; the particular components included in the composition; the age, weight, general health, sex, and diet of the animal; the animal's consumption rate, and the like. Thus, the component amounts may vary widely, and may even deviate from the proportions given herein.

The omega-3 fatty acids may be obtained from a variety of sources. One convenient source is fish oils from, for example, menhaden, mackerel, herring, anchovy, and salmon. DHA and EPA are typical fatty acids present in such fish oils, and, together often make up a significant portion of the oil, such as from about 25% to about 38% of the oil.

When the composition is an animal food, vitamins and minerals preferably are included in amounts required to avoid deficiency and maintain health. These amounts are readily available in the art. The National Research Council (NRC), for example, provides recommended amounts of such ingredients for farm animals. See, e.g., Nutrient Requirements of Swine (10th Rev. Ed., Nat'l Academy Press, Wash. D.C., 197298), Nutrient Requirements of Poultry (9th Rev. Ed., Nat'l Academy Press, Wash. D.C., 1994), Nutrient Requirements of Horses (Fifth Rev. Ed., Nat'l Academy Press, Wash. D.C., 1989), etc. And the American Feed Control Officials (AAFCO), for example, provides recommended amounts of such ingredients for dogs and cats. See American Feed Control Officials, Inc., Official publication, pp. 126-140 (2003). Examples of vitamins useful as food additives include vitamin A, B1, B2, B6, B12, C, D, E, K, H (biotin), K, folic acid, inositol, niacin, and pantothenic acid. Examples of minerals and trace elements useful as food additives include calcium, phosphorus, sodium, potassium, magnesium, copper, zinc, chloride, and iron salts.

The methods of the present invention include compositions that may further contain other additives known in the art. Preferably, such additives are present in amounts that do not impair the purpose and effect provided by the invention. Examples of additives include, for example, substances with a stabilizing effect, processing aids, substances that enhance palatability, coloring substances, and substances that provide nutritional benefits.

Stabilizing substances include, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Additives for coloring, palatability, and nutritional purposes include, for example, colorants (e.g., iron oxide, such as the red, yellow, or brown forms); sodium chloride, potassium citrate, potassium chloride, and other edible salts; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997,672. See also, U.S. Pat. No. 5,004,624. See also, U.S. Pat. No. 5,114,704. See also, U.S. Pat. No. 5,532,010. See also, U.S. Pat. No. 6,379,727. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Supplements include, for example, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, encapsulated compositions, and the like.

Treats include, for example, compositions that are given to an animal to entice the animal to eat during a non-meal time. Treats for canines include, for example, dog bones. Treats may be nutritional, wherein the composition comprises one or more nutrients, and may, for example, have a composition as described above for food. Non-nutritional treats encompass any other treats that are non-toxic.

Toys include, for example, chewable toys. Toys for dogs include, for example, artificial bones. There is a wide range of suitable toys currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). The invention provides both partially consumable toys (e.g., toys comprising plastic components) and fully consumable toys (e.g., rawhides and various artificial bones). It should be further recognized that this invention provides toys for both human and non-human use, particularly for companion, farm, and zoo animal use, and particularly for dog, cat, or bird use.

A "food" is a nutritionally complete diet for the intended recipient animal (e.g., domestic cat or domestic dog). A "nutritionally complete diet" is a diet that includes sufficient nutrients for maintenance of normal health of a healthy animal on the diet. The methods of this invention utilize compositions that are not intended to be restricted by any specific listing of proteinaceous or fat ingredients or product form. The compositions can be prepared in, for example, a dry, canned, wet, or intermediate moisture form using conventional pet food processes. In some embodiments, the moisture content is from about 10% to about 90% of the total weight of the composition. In other embodiments, the moisture content is from about 65% to about 75% of the total weight of the composition.

In preparing a composition for use with the methods of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Methods of the present invention include utilizing compositions that can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

As noted previously, this invention is directed, in part, to a method for enhancing the quality of life of an animal. The method comprises feeding a senior or super senior animal a composition in an amount effective to enhance alertness, improve vitality, protect cartilage, maintain muscle mass, enhance digestibility, and improve skin and pelage quality. The compositions are also designed to be easier to chew. Canine and feline foods are typically formulated based on life stage (age), size, body composition, and breed. In the methods of this invention, some embodiments of the compositions address specific nutritional differences between super senior regular breed dogs, large breed dogs, and cats.

All percentages expressed herein are on a weight by dry matter basis unless specifically stated otherwise.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compositions, compounds, methods, and similar information reported therein that might be used with the present invention. However, nothing herein is to be construed as an admission that the invention is not entitled to antedate such disclosure by virtue of prior invention.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

A composition formulated for senior or super senior regular breed canines is described in Table 1.

TABLE 1

Ingredient Composition for Canine Regular Breed Super Senior

| Ingredient | % of composition |
|---|---|
| Starch | 65.83 |
| Animal Protein | 14.31 |
| Vegetable Protein | 6.05 |
| Animal/Vegetable Fat | 6.60 |
| Omega Fat | 3.38 |
| Fiber | 1.42 |
| Minerals | 1.63 |
| Vitamins | 0.78 |

Example 2

A composition formulated for senior or super senior large breed canines is described in Table 2.

TABLE 2

Ingredient Composition for Canine Large Breed Super Senior

| Ingredient | % of composition |
|---|---|
| Starch | 65.15 |
| Animal Protein | 14.79 |
| Vegetable Protein | 6.45 |
| Animal/Vegetable Fat | 6.23 |
| Omega Fat | 4.12 |
| Fiber | 1.30 |
| Minerals | 0.91 |
| Vitamins | 1.05 |

Example 3

A composition formulated for senior or super senior felines is described in Table 3.

TABLE 3

Ingredient Composition for Feline Super Senior

| Ingredient | % of composition |
|---|---|
| Starch | 31.47 |
| Animal Protein | 25.57 |
| Vegetable Protein | 20.14 |
| Animal/Vegetable Fat | 13.31 |
| Omega Fat | 1.61 |
| Fiber | 4.80 |
| Minerals | 1.77 |
| Vitamins | 1.34 |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for enhancing the quality of life of a senior or super senior animal comprising feeding the animal a composition comprising: at least about 9% by weight protein; at least about 5% by weight fat; and at least about 0.05% by weight of at least one omega-3 polyunsaturated fatty acid, wherein enhanced quality of life is evidenced by an improvement in one or more characteristics selected from the group consisting of cartilage protection, maintenance of muscle mass and skin quality.

2. The method of claim 1 wherein the method comprises feeding the animal the composition in an amount effective to protect cartilage.

3. The method of claim 1 wherein the method comprises feeding the animal the composition in an amount effective to maintain muscle mass.

4. The method of claim 1 wherein the method comprises feeding the animal the composition in an amount effective to improve skin quality.

5. The method of claim 1 wherein the animal is selected from the group consisting of a cat, a dog, and a horse.

6. A method for enhancing the quality of life of a senior or super senior animal comprising feeding the animal a composition comprising: at least one omega-3 polyunsaturated fatty acid selected from the group consisting of docosahexaenoic acid and eicosapentaenoic acid; at least one antioxidant; and at least one nutrient selected from the group consisting of choline, manganese, methionine, cysteine, L-carnitine, lysine, and mixtures thereof, wherein the composition comprises at least about 500 ppm vitamin E, at least about 50 ppm vitamin C and at least about 600 ppm taurine, and wherein enhanced quality of life is evidenced by an improvement in one or more characteristics selected from the group consisting of cartilage protection, maintenance of muscle mass and skin quality.

7. The method of claim 6 wherein the omega-3 polyunsaturated fatty acid in the composition is DHA and wherein the composition comprises at least about 0.02% by weight DHA as measured on a dry matter basis.

8. The method of claim 6 wherein the omega-3 polyunsaturated fatty acid in the composition is DHA and wherein the composition comprises from about 0.02% to about 0.40% by weight DHA as measured on a dry matter basis.

9. The method of claim 6 wherein the omega-3 polyunsaturated fatty acid in the composition comprises EPA and wherein the composition comprises at least about 0.1% by weight EPA as measured on a dry matter basis.

10. The method of claim 6 wherein the omega-3 polyunsaturated fatty acid in the composition comprises EPA, and wherein the composition comprises from about 0.1% by weight to about 1% by weight EPA as measured on a dry matter basis.

11. The method of claim 6 wherein the omega-3 polyunsaturated fatty acid in the composition comprises a mixture of DHA and EPA, and wherein the composition comprises at least about 0.02% by weight DHA and at least about 0.1% by weight EPA on a dry matter basis.

12. The method of claim 6 wherein the composition comprises one or more antioxidants selected from the group consisting of vitamin E, vitamin C, taurine, beta-carotene, carnitine, lipoic acid, and cystine.

13. The method of claim 6, wherein the composition further comprises at least about 1000 ppm choline.

14. The method of claim 6 wherein the composition fed to the animal is an animal treat or an animal toy.

15. The method of claim 6 wherein the composition fed to the animal is a nutritional supplement.

16. A method for enhancing the quality of life of a senior or super senior small or regular breed canine comprising feeding the animal a composition comprising: from about 60% to about 70% by weight starch; from about 15% to about 25% by weight protein selected from the group consisting of animal protein and vegetable protein; from about 5% to about 7% by weight fat selected from the group consisting of animal fat and vegetable fat; from about 2.5% to about 4% by weight of at least one omega-3 polyunsaturated fatty acids; from about 1% to about 2% by weight fiber; from about 1% to about 2% by weight minerals; and from about 0.5 to about 1.5% by weight vitamins, wherein enhanced quality of life is evidenced by an improvement in one or more characteristics selected from the group consisting of cartilage protection, maintenance of muscle mass and skin quality.

17. A method for enhancing the quality of life of a senior or super senior large breed dog, wherein the method comprises feeding the animal a composition comprising: from about 60% to about 70% by weight starch; from about 15% to about 25% by weight protein selected from the group consisting of animal protein and vegetable protein; from about 5% to about 7% by weight fat selected from the group consisting of animal fat and vegetable fat; from about 3% to about 5% by weight of at least one omega-3 polyunsaturated fatty acids; from about 1% to about 1.5% by weight fiber; from about 0.5% to about 1% by weight minerals; and from about 0.75 to about 1.25% by weight vitamins, wherein enhanced quality of life is evidenced by an improvement in one or more characteristics selected from the group consisting of cartilage protection, maintenance of muscle mass and skin quality.

18. A method for enhancing the quality of life of a senior or super senior cat, wherein the method comprises feeding the animal a composition comprising: from about 30% to about 35% by weight starch; from about 40% to about 50% by weight protein selected from the group consisting of animal protein and vegetable protein; from about 12% to about 15% by weight fat selected from the group consisting of animal fat and vegetable fat; from about 1% to about 2% by weight of at least one omega-3 polyunsaturated fatty acids; from about 3% to about 5% by weight fiber; from about 1% to about 2% by weight minerals; and from about 1% to about 2% by weight vitamins, wherein enhanced quality of life is evidenced by an improvement in one or more characteristics selected from the group consisting of cartilage protection, maintenance of muscle mass and skin quality.

\* \* \* \* \*